United States Patent [19]
Otto-Nagels

[11] Patent Number: 5,725,123
[45] Date of Patent: Mar. 10, 1998

[54] SYSTEM FOR CLOSING CONTAINERS

[75] Inventor: Hans Otto-Nagels, Bovenden, Germany

[73] Assignee: Heraeus Instruments GmbH, Hanau, Germany

[21] Appl. No.: 805,653

[22] Filed: Feb. 27, 1997

[30] Foreign Application Priority Data

Sep. 2, 1996 [DE] Germany ................. 196 08 009.6

[51] Int. Cl.[6] ................................. B65D 43/08
[52] U.S. Cl. ..................... 220/796; 220/4.21; 215/230; 215/317
[58] Field of Search ........................... 215/206, 230, 215/317; 220/281, 796, 799, 4.21

[56] References Cited

U.S. PATENT DOCUMENTS

| | | | |
|---|---|---|---|
| 885,682 | 4/1908 | Zimmerman | 220/796 X |
| 1,720,835 | 7/1929 | Holmdahl | 215/317 |
| 2,677,647 | 5/1954 | Lovell. | |
| 3,071,275 | 1/1963 | Foss et al. | 215/317 |
| 3,995,766 | 12/1976 | Fralick | 220/282 |
| 4,828,130 | 5/1989 | Hofmann | 215/317 |
| 5,657,895 | 8/1997 | Rogge | 220/366.1 |

FOREIGN PATENT DOCUMENTS 3017354  11/1981  Germany.
3128542   4/1982  Germany.

Primary Examiner—Stephen Cronin
Attorney, Agent, or Firm—Workman, Nydegger & Seeley

[57] ABSTRACT

The present invention concerns a system for closing cylindrical containers, such as Petri dishes, for example, with a cover cap whose cover apron presses against the outer surface of the lateral wall of the container. In particular, the present invention provides a cylindrical container and cover system having a simple and convenient, yet secure, closing and opening mechanism which consists of as few individual parts as possible. The cover cap of the present invention has individual elevations on the inner surface of the cover apron. The elevations press against the outer surface of the container walls to hold it in a non-positive manner. The elevations are made as knobs or elongated struts, and are arranged on opposite circular sections of the cover apron in such a way that at least two opposite sections of at least 130° of the periphery of the cover apron have no elevations. In accord with the invention, a simple mechanism for removing the cover cap from the container is also provided. Gripping surfaces are provided on the cover apron at positions approximately 90° to the elevations which permit the cover cap to be loosened from the container and lifted off with a simple and convenient maneuver.

6 Claims, 3 Drawing Sheets

SYSTEM FOR CLOSING CONTAINERS

BACKGROUND OF THE INVENTION

1. The Field of the Invention

This invention concerns a system for closing cylindrical containers, such as Petri dishes, for example, with a cover cap whose cover apron presses against the outer surface of the lateral wall of the container.

2. Related Applications

Foreign priority benefits under Section 119 of Title 35 of the United States Code of German Utility Model Application No. 196 08 009.6, filed Mar. 4, 1996, incorporated herein by reference, are claimed for this application.

3. The Relevant Technology

Cylindrical containers, such as Petri dishes, for example, are well known, particularly for laboratory applications. Typically, these containers consist of a flat, circular dish with a vertical wall and a circular cover cap, whose cover apron is slightly conical, and therefore lies only loosely upon the lower dish. German patent DE 31 28 542 describes a sealed closure for a container similar to the type described. In this case, the container displays a peripheral thickening on its top edge which serves to secure an elastic sealing ring pressing on the vertical wall of the container. The sealing ring, in rum, also has a peripheral bulge outside which snaps into the recess on the inner surface of the cover apron when the lower dish is closed with the cover cap. Therefore, this known system consists of three specially molded parts. Although the system provides excellent sealing, the peripheral sealing ring makes it difficult to lift the cover cap off with only one hand, particularly for larger containers. In addition, the excellent sealing property is not always advantageous since strong sealing is not desired for some applications of these containers.

SUMMARY AND OBJECTS OF THE INVENTION

It is an object of the present invention to provide a cylindrical container and cover system having a simple, convenient, yet secure closing and opening mechanism.

It is a further object of the present invention to provide a cylindrical container and cover system consisting of as few individual parts as possible.

These and other objects and features of the present invention will become more fully apparent from the following description and appended claims, or may be learned by the practice of the invention as set forth hereinafter.

The present invention concerns a system for closing cylindrical containers, such as Petri dishes, for example, with a cover cap whose cover apron presses against the outer surface of the lateral wall of the container. In particular, the present invention provides a cylindrical container and cover system having a simple and convenient, yet secure, closing and opening mechanism which consists of as few individual parts as possible. The cover cap of the present invention has individual elevations on the inner surface of the cover apron. The elevations press against the outer surface of the container walls to hold it in a non-positive manner. The elevations are made as knobs or elongated struts, and are arranged on opposite circular sections of the cover apron in such a way that at least two opposite sections of at least 130° of the periphery of the cover apron have no elevations. In accord with the invention, a simple mechanism for removing the cover cap from the container is also provided. Gripping surfaces are provided on the cover apron at positions approximately 90° to the elevations which permit the cover cap to be loosened from the container and lifted off with a simple and convenient maneuver.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
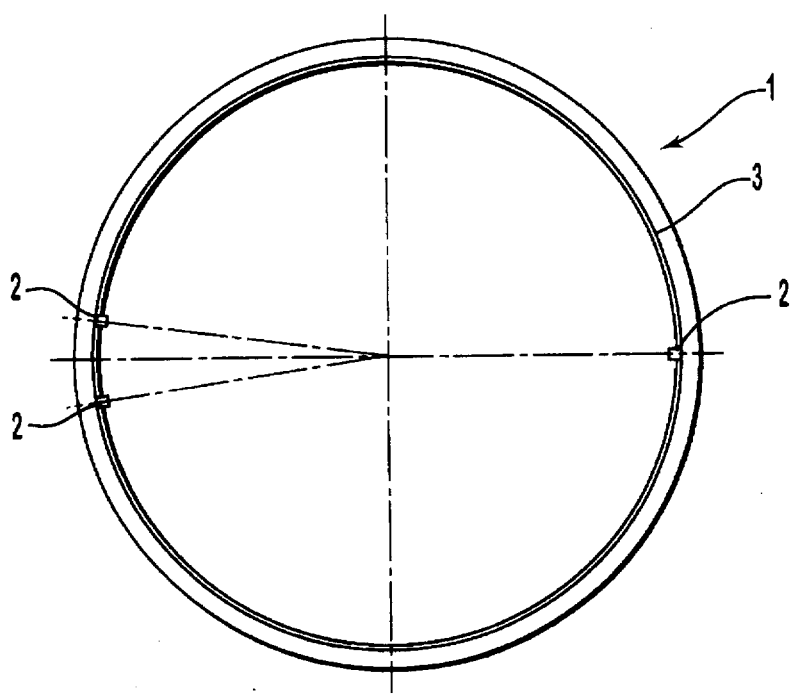
FIG. 1 is a bottom view of a cover cap with a total of three elevations on the cover apron.

The present invention concerns a system for closing cylindrical containers, such as Petri dishes, for example, with a cover cap whose cover apron comprises elevations for pressing against the outer surface of the lateral wall of the container. In particular, the present invention provides a cylindrical container and cover system having a simple and convenient, yet secure, closing and opening mechanism which consists of as few individual parts as possible.

The cover cap of the present invention has at least one elevation on the inner surface of the cover apron. The elevation(s) press against the outer surface of the lateral wall of the container to hold it in a non-positive manner. It is advantageous if the elevations of the cover apron press against the outer surface of the lateral wall of the regular cylindrical container rather than outside on the bottom surface of the container. Typically, more than one elevation is desired, particularly for larger containers. If the cover apron has more than one elevation, these can be arranged opposite one another in pairs or larger groupings to ensure that two opposite sections of at least 130° of the periphery of the cover apron have no elevations.

The elevations can have different shapes. The elevations are preferably made as knobs or elongated struts and are preferably arranged on the inner surface of opposite circular sections of the cover apron in such a way that two opposite sections of at least 130° of the periphery of the cover apron have no elevations. Generally, fewer elevations are suitable for smaller and lighter containers while more elevations are needed for larger and heavier containers. For large volume containers which may be heavy, it is preferred to use four pairs of elevations, i.e., eight individual elevations.

Although an elevation formed as a continuous peripheral bulge, as known in the art, provides means for closing the container, opening the container may be difficult. This type of system requires a greater force or, as disclosed, for example, in German patent DE 31 28 542, requires a specially shaped elastic sealing ring. In contrast, the present invention provides a simple mechanism for removing the cover cap from the container. In addition, additional parts, such as a sealing ring, are not required.

The mechanism for opening the system according to the invention is shown very simply by gripping the cover apron with one hand rotated approximately 90° to the elevations and gently pressing on the cover cap. This "pliers grip" pulls the elevations which have been pressing against the outer surface of the lateral wall of the container back from the container to thereby release the container. This mechanism can only be ensured in a repeatable manner if the material of the cover apron has resilient properties which are provided by numerous known plastic materials including those typically used for container and cover systems.

In order to locate the correct point for gripping the described opening mechanism, the cover cap preferably has gripping surfaces marked on it. These markings can be any known and useful markings such as a colored symbol, roughened or textured surfaces portions, or writing placed on the cover apron and/or the cover cap surface.

In a preferred embodiment, the gripping surfaces are marked on the resilient cover apron and/or the cover cap at positions approximately 90° to the elevations which permits the cover cap to be loosened from the container and lifted off with the simple and convenient maneuver as described above. In contrast, for transporting the container with the cover secured in place, the container can be lifted by gripping the cover apron or cover cap in the area of the elevations. In this manner, the pressing of the elevations against the outer surface of the lateral wall of the container is maintained to ensure that the cover will not be lifted from the container. It will be appreciated that the system of the present invention is very practical and convenient for personnel working in a laboratory or other such environment.

Figure 6:
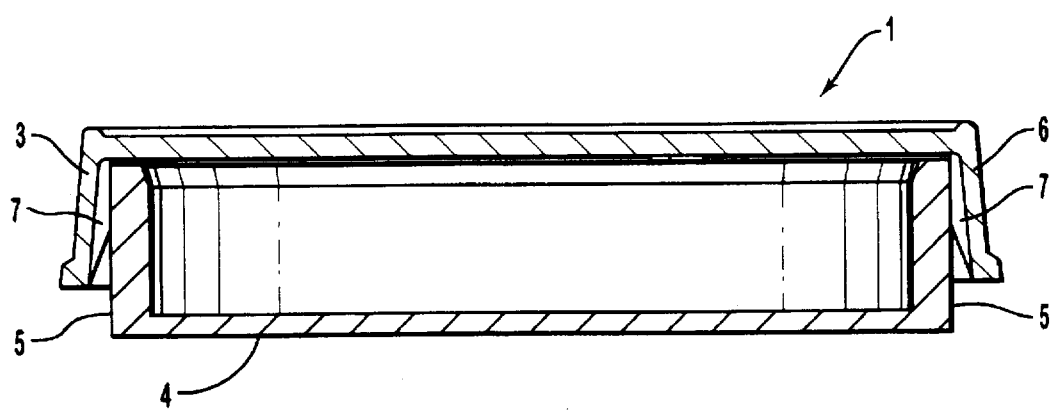
FIG. 6 is a sectional drawing of an embodiment comprising a singular cylindrical container and a cover cap.
Figure 7:
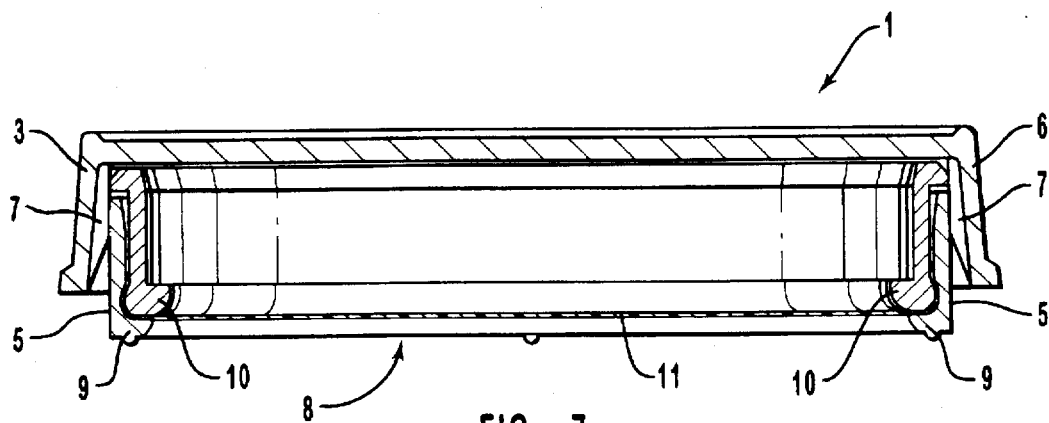
FIG. 7 is a sectional drawing of an embodiment comprising a two-part cylindrical container and a cover cap.

FIG. 1 shows a cover cap 1 with three elevations 2 on the inner surface of its cover apron 3 to secure the closure of a container such as the unitary container 4 shown in FIG. 6 or the two-part container 8 shown in FIG. 7. Due to the relatively small number of elevations 2 which press against the outer surface of the lateral wall of a container, the illustrated embodiment would preferably be used with smaller and, therefore, lighter containers.

Figure 2:
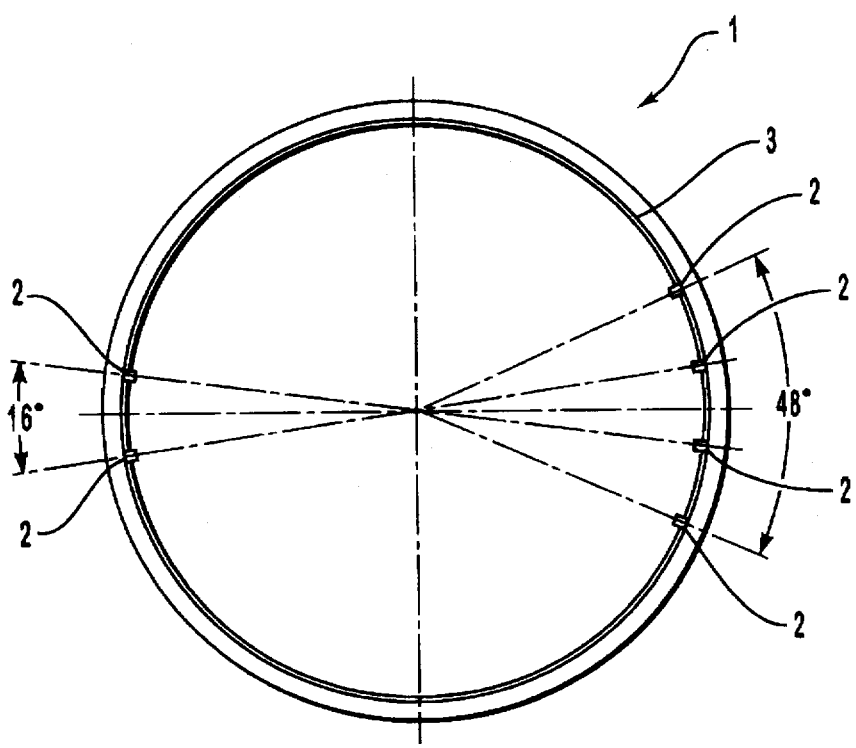
FIG. 2 is a bottom view of a cover cap as shown in FIG. 1 but having a total of six elevations wherein two pairs of elevations lie opposite one another.

FIG. 2 represents another embodiment of a cover cap 1 in accord with the present invention having a total of six elevations 2 on the inner surface of the cover apron 3 to secure the closure of a container such as the unitary container 4 shown in FIG. 6 or the two-part container 8 shown in FIG. 7. Due to the larger number of elevations 2 which press against the outer surface of the lateral wall of a container, the illustrated embodiment would be suitable for use with relatively larger and heavier containers than the embodiment illustrated in FIG. 1.

Figure 3:
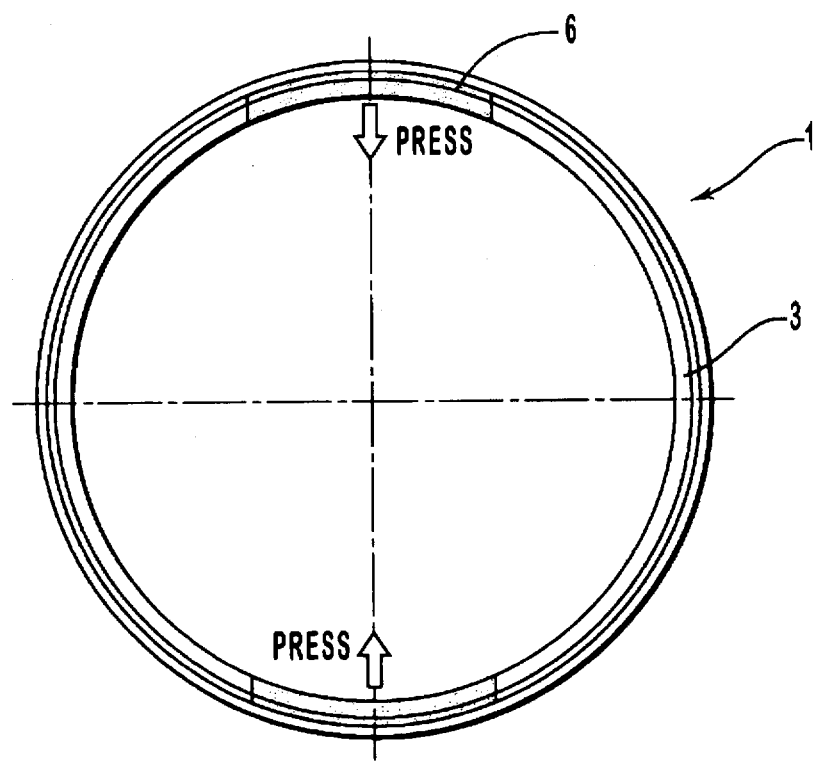
FIG. 3 is a top view of a cover cap with marked gripping surfaces lying opposite one another.
Figure 4:
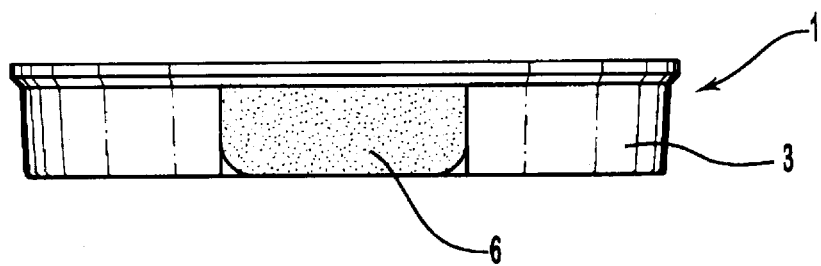
FIG. 4 is a side view of the cover cap shown in FIG. 3.

FIGS. 3 and 4 illustrate a cover cap 1 such as the cover cap shown in FIGS. 1 or 2 when viewed from the outside. Accordingly, the elevations 2 on the inner surface of the cover apron 3 are not visible in FIGS. 3 and 4. As shown in FIGS. 3 and 4, gripping surfaces 6 are positioned approximately 90° from the elevation positions. The gripping surfaces 6 are preferably identified by means such as surface-structure markings on the cover apron 3 and/or by writing "PRESS" above an arrow indicating the direction for pressing on the cover cap surface.

Figure 5:
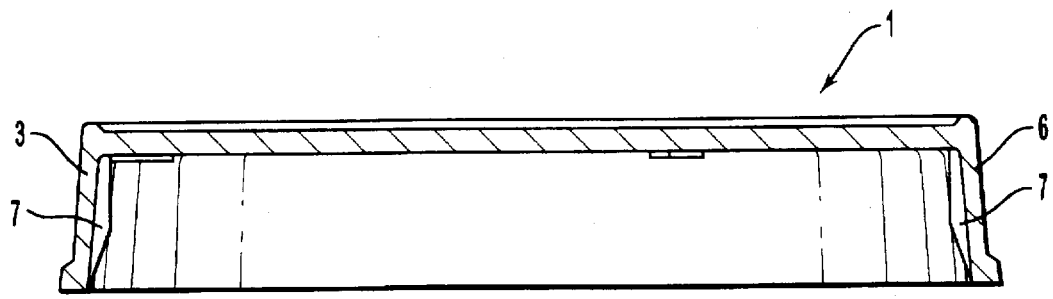
FIG. 5 is a sectional drawing of a cover cap with elevations on the cover apron.

FIG. 5 shows a cover cap 1 in sectional view to illustrate a preferred configuration for the elevations as elongated struts 7 on the inner surface of the cover apron 3. It will be appreciated that other configurations, such as knobs, would also be suitable for the elevations.

FIG. 6 shows an embodiment of a unitary regular cylindrical container 4, such as a Petri dish, closed by a cover cap 1 in sectional view. The cover cap 1 comprises elevations 2 preferably configured as elongated struts 7 on the inner surface of the cover apron 3 which press upon the outer surface of the lateral wall 5 of container 4.

FIG. 7 shows an embodiment of a two-part container 8 closed by a cover cap 1 in sectional view. The two-part container 8 comprises an outer and an inner concentric frame element, 9 and 10, respectively. The two concentric frame elements secure a plastic film 11 forming the floor of the container. Such two-part containers are commonly used for many laboratory applications. The cover cap 1 comprises elevations 2 preferably configured as elongated struts 7 on the inner surface of the cover apron 3 which press upon the outer surface of the lateral wall 5 of outer concentric frame 9.

As seen in FIGS. 3 and 4, marked gripping surfaces are preferably arranged on the outside of cover apron 3 and/or on the outside of the cover cap surface. Pressing cover cap 1 together at the marked positions allows the cover to be easily lifted off a container. It will be appreciated that a cover cap as disclosed herein could be useful for various types of containers.

It is a feature of the present invention that the elevations are positioned such that relatively large portions of the periphery of the cover apron have no elevations. As shown in FIG. 2, the circular angular section of 48° on the arc described by four of the elevations 2 represents a tolerance limit for the easy opening mechanism of the present invention. Pressing on the cover cap 1 in the areas of the marked gripping surfaces as shown in FIGS. 3 and 4 allows the cover to be lifted from the container. Moreover, persons using the container and cover system can perform this opening maneuver with only one hand using the "pliers grip". It will be appreciated that, if desired, the six elevations could be arranged symmetrically on two opposite sections of the periphery of the cover apron such that each of the opposed sets of three elevations describes a circular angular section having an arc of 48°.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A system for closing cylindrical containers comprising a cover cap, said cover cap comprising a cover surface, gripping surfaces, markings corresponding to said gripping surfaces, and a cover apron, said cover apron having an inner periphery surface and at least one elevation on the inner periphery surface of said cover apron, said at least one elevation positioned such that two opposite sections of the inner periphery surface describing arcs of at least 130° have no elevations thereon, wherein said at least one elevation can be pressed against an outer surface of said cylindrical container to thereby securely cover the container in a non-positive manner.

2. The system for closing cylindrical containers described in claim 1 wherein two gripping surfaces are arranged opposite one another on the cover apron at an angular distance of 180° and no elevations or gripping surfaces are positioned within two pairs of circular angular sections lying opposite one another on the cover apron, each circular angular section describing an arc of at least 45°.

3. The system for closing cylindrical containers described in claim 1 wherein said markings corresponding to said gripping surfaces are achieved by the application to the cover surface or the cover apron of marks selected from the group consisting of colored symbols, notch points, depressions, surface texture modifications, and writing, and combinations thereof.

4. The system for closing cylindrical containers described in claim 1 wherein said elevations extend from said inner periphery surface of said cover apron at a right angle to said cover surface.

5. The system for closing cylindrical containers described in claim 1 wherein said elevations extend from said inner periphery surface of said cover apron parallel to said cover surface.

6. The system for closing cylindrical containers described in claim 1 wherein the number of elevations does not exceed four.

* * * * *

UNITED STATES PATENT AND TRADEMARK OFFICE
CERTIFICATE OF CORRECTION

PATENT NO. : 5,725,123
DATED : March 10, 1998
INVENTOR(S) : Hans Otto-Nagels

It is certified that error appears in the above-identified patent and that said Letters Patent is hereby corrected as shown below:

Title page,
Item [56], References Cited, FOREIGN PATENT DOCUMENTS, change "Sep. 2, 1996" to -- Mar. 4, 1996 --.

Column 1,
Line 25, change "rum" to -- turn --.

Signed and Sealed this

Tenth Day of August, 2004

JON W. DUDAS
*Acting Director of the United States Patent and Trademark Office*